United States Patent [19]

Kugler et al.

[11] Patent Number: 4,998,818
[45] Date of Patent: Mar. 12, 1991

[54] OPHTHALMOSCOPE WITH LINEAR POLARIZER

[75] Inventors: Andrew J. Kugler, Syracuse; Thaddeus J. Wawro, Auburn, both of N.Y.

[73] Assignee: Welch Allyn, Inc., Skaneateles Falls, N.Y.

[21] Appl. No.: 397,269

[22] Filed: Aug. 23, 1989

[51] Int. Cl.$^5$ .............................................. A61B 3/10
[52] U.S. Cl. .................................... 351/205; 351/218
[58] Field of Search ................ 351/205, 215, 218, 221

[56] References Cited

U.S. PATENT DOCUMENTS 3,501,228  3/1970  Speelman ............................ 351/218
4,526,449  7/1985  Newman et al. ..................... 351/205
4,643,546  2/1987  Richards ............................. 351/205

FOREIGN PATENT DOCUMENTS 270387  of 1988  Fed. Rep. of Germany .
2204144 of 1988  United Kingdom .

Primary Examiner—Paul M. Dzierzynski
Attorney, Agent, or Firm—Wall and Roehrig

[57] ABSTRACT

An ophthalmoscope is provided with a slidably mounted rack which carries two polarizing filters mounted at right angles to each other so as to simultaneously position one filter in the light path and the other in the viewing path. The rack also carries a clear lens and a red-free filter for optional positioning in the light path.

15 Claims, 3 Drawing Sheets

OPHTHALMOSCOPE WITH LINEAR POLARIZER

Background of the Invention

This invention relates to medical diagnostic instruments and more particularly to an ophthalmoscope having a linear light polarizer mechanism for selectively polarizing light for viewing a patient's eye.

Many prior art ophthalmoscopes provide a choice of apertures, filters, and one or more lens discs that can be manually rotated to bring a selected lens combination into registry with the physician's viewing path through the instrument. The closer the light transmission path and the reflected viewing light path come to being coaxial, the greater the reflected light from the patient's cornea will be. Accordingly, with ophthalmoscopes of the type herein disclosed, it is important to provide glare attenuation devices. Since light reflected off the shiny surface of the cornea will retain its polarization and light reflected from the retina loses its polarization, the glare can be virtually eliminated by passing the illuminating light through a first polarizer and the reflected light through a second polarizer. Some instruments in the past have offered a polarized viewing mode in which a circular light polarizer is shifted into the common portion of the light transmission path and the physician's viewing path to reduce glare caused by light reflected off the cornea of the patient's eye. Others have provided first and second polarizers shifted into the light transmission path and the physician's viewing path, respectively, by individual actuators to provide for polarized light viewing of the patient's eye and elimination of reflected glare.

The circular light polarizer, which comprises a linear polarizer and one-quarter wave plate, is less efficient in attenuating the glare from corneal reflections and the separate controls for the dual polarizers are inconvenient compared to the present invention.

It has been found desirable to increase the utility and range of examination options for the physician by providing a simplified automatic system for permitting viewing with polarized light or with red-free light or with standard aperture selection as desired by the physician. To the best of applicant's knowledge, this has not been provided heretofore.

OBJECTS AND SUMMARY OF THE INVENTION

The ophthalmoscope of the present invention is generally similar to the configuration shown in U.S. Pat. No. 4,526,449 to Richard W. Newman et al., and U.S. Pat. No. 4,643,546 to Byron Richards, which have been assigned to a common assignee, together with the present application. In addition to the single or dual lens discs and the normal aperture selection means of the referenced patents, applicant now provides a second aperture modification assembly that permits the physician to additionally select red-free light illumination and polarized or non-polarized light illumination of the patient's eye in a more convenient fashion. According to the present invention, by operation of a simple slider switch, the physician is able to switch into the optical path two polarizers, a lens or aperture, or a filter.

Accordingly, it is an object of the present invention to provide an ophthalmoscope with a linear light polarizer assembly that can be simply and easily positioned in and out of the illumination and viewing path of the ophthalmoscope.

It is another object of the present invention to provide a single function control for converting an ophthalmoscope from regular to dual polarized viewing.

It is another object of the present invention to provide an ophthalmoscope with an improved light polarizing system.

It is a further object of the present invention to virtually eliminate corneal reflections in coaxial illumination and viewing ophthalmoscopes.

These and other and further objects of the present invention, together with additional features contributing thereto and advantages accruing therefrom will be apparent from the following description of a preferred embodiment shown in the accompanying drawing with like reference numerals indicating corresponding parts throughout wherein:

BRIEF DESCRIPTION OF THE DRAWING

FIG. 4 is an exploded perspective view of the mirror and mounting assembly, together with the aperture rack and actuating controls therefore; and FIG. 5 is a perspective view of the actuator mechanism for positioning the light polarizer into and out of the illumination path.

DETAILED DESCRIPTION OF THE PREFERRED EMBODIMENT

Figure 1:
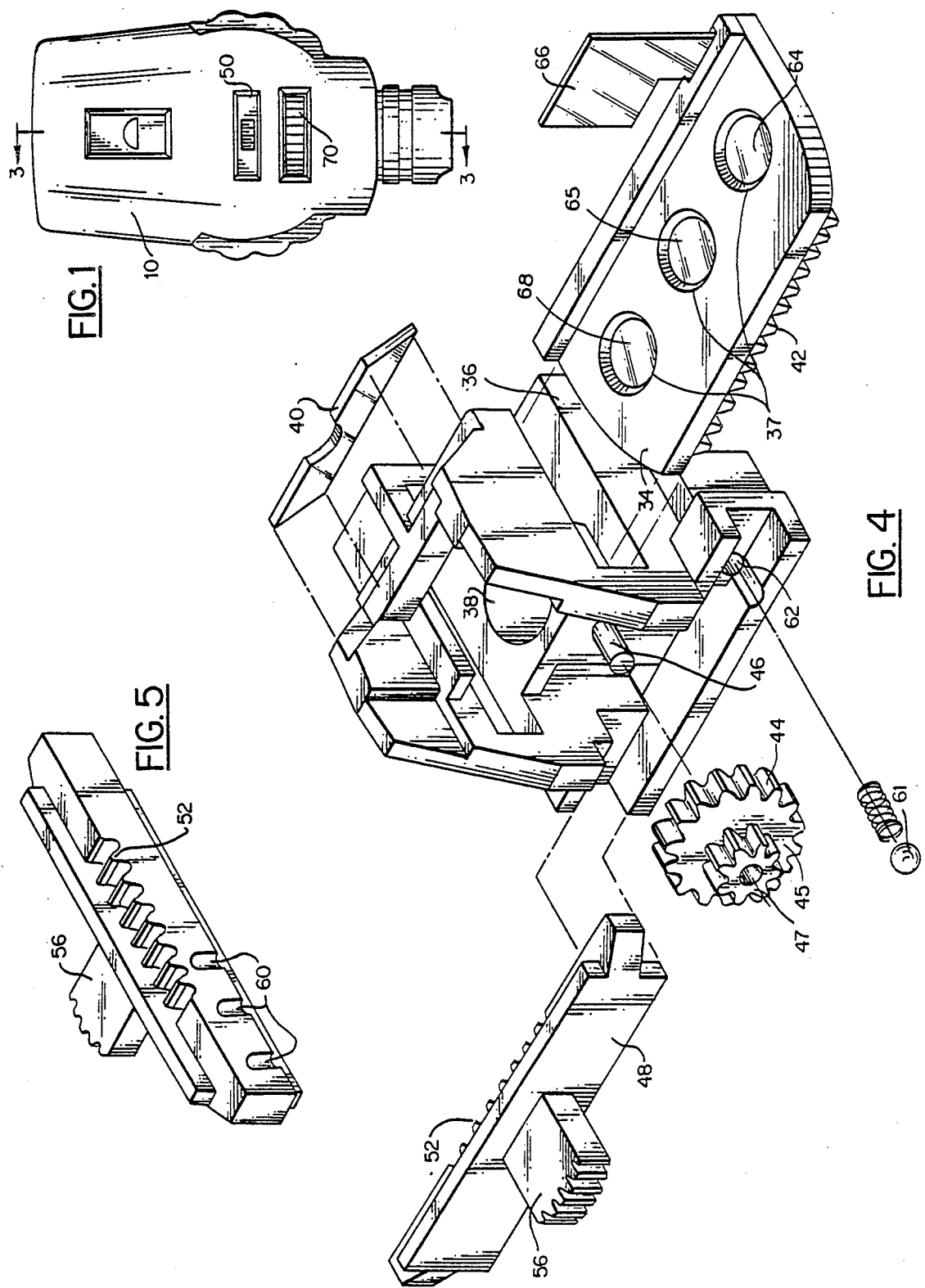
FIG. 1 is a front elevation view of the patient's side of the ophthalmoscope of the present invention.
Figure 2:
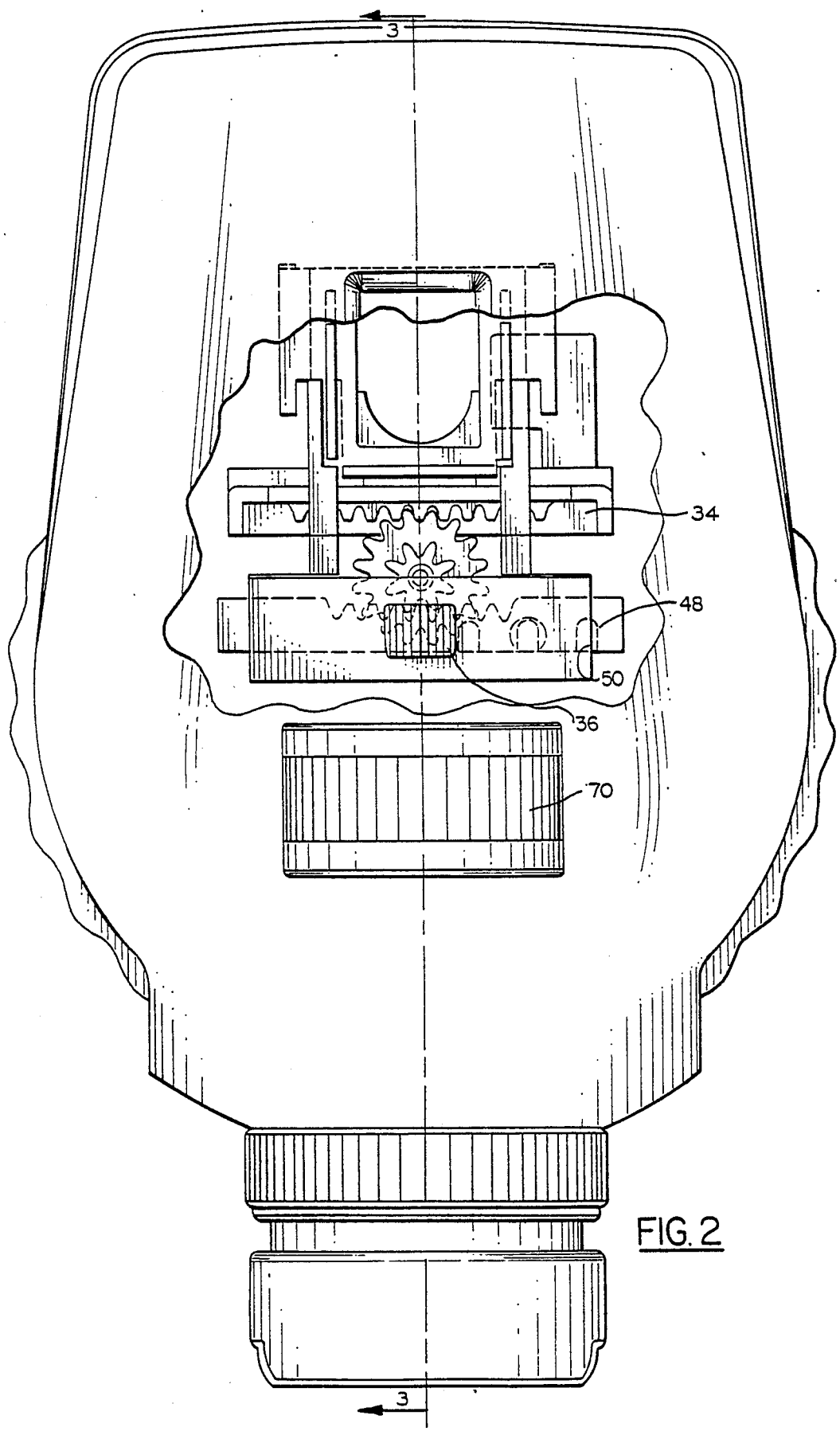
FIG. 2 is an enlarged and partially broken away sectional view of the device of FIG. 1.
Figure 3:
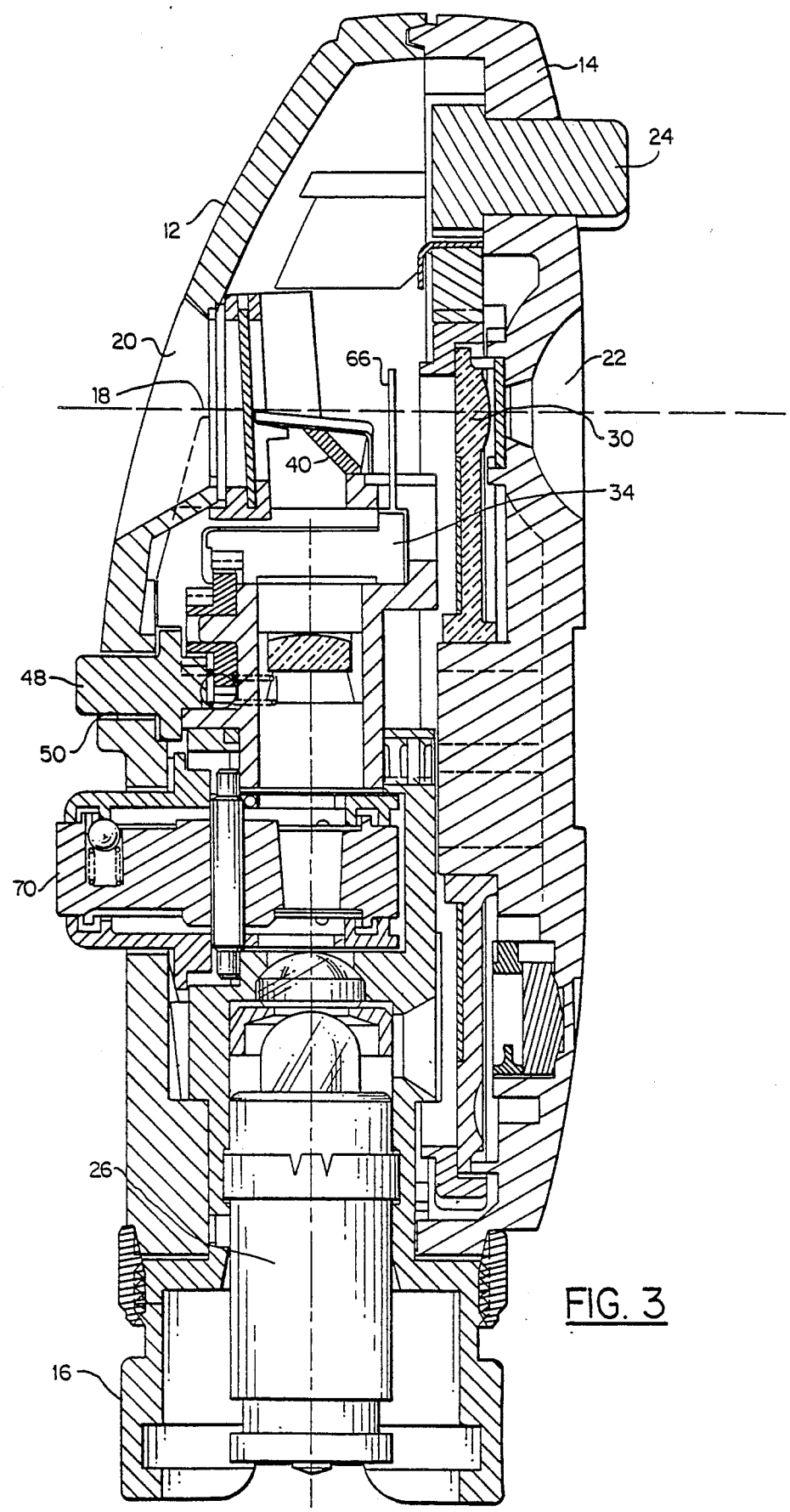
FIG. 3 is a sectional view taken along line 3—3 of FIG. 2.

Referring now to FIGS. 1-3 the ophthalmoscope 10 according to the present invention has a main body portion 12 and a main cover 14 which together form the housing for the instrument. The main body base 12 contains most of the elements of the optical system and has a neck 16 that is adapted to be releasably connected to a conventional battery handle, not shown. A viewing passage indicated by phantom line 18 in FIG. 3 extends transversely through the instrument and this passage terminates at the front of the instrument in a viewing opening 20 and at the rear of the instrument in an eye opening 22 for the physician. The usual resilient bumper for positioning the instrument on the physician's brow is provided at 24 and a light source 26 is provided in the neck of the instrument powered by the battery handle, not shown. Light source 26 preferably consists of a curved filament bulb as disclosed in the above patent '449 that permits a virtual coaxial alignment of the illumination path and the viewing path to eliminate as many annoying shadows as possible. A single rotatable lens disc 30 is provided and aperture rack 34 is provided for carrying the polarizer system, an open aperture and a filter.

As may be seen in FIG. 4, the aperture rack 34 is slidably mounted within the mirror holder 36 so that the lenses and/or filters positioned in apertures 37 in rack 34 may be positioned within the light transmission path at 38. Light transmitted therethrough to the reflecting mirror 40 is used to illuminate the patient's eye. Unfiltered light is used for general viewing of the eye while the red-free filter is used to examine veins and nerve fiber layers on the back of the retina and the polarized light is useful in examining the retina with minimum reflected glare from the cornea. This is especially useful when the patient's eye is undilated.

Aperture rack 34 has a rack gear 42 on the bottom edge thereof which, when in the assembled position, engages with the gear 44 mounted on shaft 46. Gear 44 has two sections: a larger diameter section 45 having sixteen teeth for moving the aperture rack 34 and a smaller diameter section 47 having eight teeth adapted to engage rack gear 52 on actuator switch 48.

The actuator switch 48 is mounted outwardly of the gear 44 and extends through an opening 50 in the casing 12 shown in FIGS. 1-3. The switch actuator 48 is a flat bar having a rack gear 52 on the upper surface thereof positioned to engage the smaller diameter section 47 of the spur gear 44. The bar 48 may be moved laterally from left to right by applying pressure on lug 56. This rotates the small spur gear 47 which, through section 45 of gear 44, moves the aperture rack 34 back and forth in FIG. 4.

In addition, as may be seen in FIG. 5, there are three detentes 60 adapted to engage a spring urged ball 61 mounted in a recess 62 in the mirror holder 36, as may be seen in FIG. 4. These detentes and spring urged ball provide three fixed positions for the actuator bar 48 which correspond with the three locations where the apertures 37 of the aperture rack 34 are properly aligned with the opening 38 in the mirror holder 36 for proper transmission of light from the light source to the mirror and into the patient's eye.

The light polarizing mechanism of the present invention consists of two polarizers, 64 and 66. Polarizer 64 is positioned in the right hand aperture in aperture rack 34 and polarizes the light transmitted from the light source 26 to mirror 40 and thence to the patient's eye. Polarizing element 66 is mounted at right angles to the polarizer 64 in the edge of rack 34 and is positioned behind mirror 40 to be in the line of sight 18 of the physician's viewing path. Polarizer 66 is mounted with its polarization axis at 90 degrees to the polarization axis of polarizer 64 so as to prevent light reflected from the patient's cornea from reaching the physician's eye. This may also be seen in FIG. 3.

This is accomplished by moving the aperture rack 34 to its extreme left-hand position in FIGS. 2 and 4, by actuating the actuator bar 48 to its full right-hand position to engage spring biased ball 61 in the detente at the extreme right-hand side in FIG. 5. Conversely, when the red free filter, which is located in the extreme left-hand aperture of rack 34 is to be positioned in alignment with aperture 38, the actuator bar 48 is moved to the left-hand position in FIG. 4, which rotates the gear 44 to bring the aperture rack to its full right-hand position. The extreme left-hand detente 60 (FIG. 5) then engages the ball 61 and retains the filter in position. If normal light is desired, the actuator bar is positioned approximately half-way between to align the central aperture on the aperture rack 34 with the aperture 38 for normal light transmission. This action can be seen more clearly in FIG. 2 where the slide bar 48 is shown in phantom lines.

The light polarizer 64, the standard clear lens or aperture 65, and the red free lens 68 are mounted in recesses on the under side of apertures 37 in aperture rack 34. In addition to these devices, there are the standard aperture openings positioned below the mirror holder 36 and controlled by the actuating dial 70 which may be seen in FIGS. 1 and 2.

It will thus be seen that the physician can easily and quickly adjust the ophthalmoscope to the desired light conditions by a single setting of the actuator bar 48 to the desired position. In the polarized light mode, the advantages of dual polarizing filters are obtained with a single setting, permitting the physician to examine the patient's eye in the most efficient and thorough manner.

While the invention has been described in the specification and illustrated in the drawings with reference to a preferred embodiment, it will be understood by those of skill in the art that various changes may be made and equivalents may be substituted for elements of the invention without departing from the scope of the claims.

What is claimed is:

1. In an ophthalmoscope having a housing, a viewing passage therethrough, and an illumination source positioned to project a beam of light through said viewing passage; means for selectively modifying the light projected through said passage and the light observed through said passage comprising:

a frame member mounted in said housing adjacent the viewing passage and the illumination source beam of light;

a plurality of light filtering members disposed in said frame member; and single actuating means for selectively positioning said frame member to align one light filtering member in the illumination source beam of light and another light filtering member in said viewing passage.

2. An ophthalmoscope as claimed in claim 1 further defined by said frame member including an aperture member slidably mounted therein and at least one of said light filtering members being a light polarizer.

3. An ophthalmoscope as claimed in claim 2 wherein said aperture member has formed therein a plurality of filter openings; a different light filter member disposed in each of said openings, and at least one other light filter member disposed adjacent to and in perpendicular relationship to one of said light filter members.

4. A device as described in claim 3 wherein said different light filter members comprise a red free filter member, a first light polarizing filter member, and a clear filter member mounted in said filter openings for selective positioning in the light transmitted to the patient's eye.

5. An ophthalmoscope as claimed in claim 1 further characterized by a first and a second light filter member disposed adjacent each other, with said second light filter member being disposed in a plane at an angle to the plane of said first filter member, so that when said first filter member is positioned in the light transmitted to the patient's eye, the second filter is positioned in the viewing passage to the physician's eye to filter light reflected from the patient's eye.

6. A device as described in claim 1 wherein said plurality of light filtering members include a first light polarizing member mounted in said frame member and a second light polarizing member mounted adjacent to said first light polarizing member in said frame member at an angle to said first polarizer and such that the polarization axes are perpendicular.

7. A device as claimed in claim 1 wherein said frame member includes a plurality of circular openings; a rack gear along one edge and a polarizing member mounting slot along the edge opposite said rack gear;

said actuating means comprises a switch actuator bar having thereon a finger actuator portion and a rack gear portion; and a spur gear rotatably mounted in said frame to operatively connect said frame member to said switch actuator bar.

8. In an ophthalmoscope having a housing, a viewing passage therethrough, a light source, lens and mirror light transmission means disposed to transmit a beam of light from said source through said viewing passage to the patient's eye, and light filtering means comprising:
an aperture rack member movably mounted in said housing;
a plurality of light filter members disposed in said rack member characterized by first and second light filter members disposed adjacent to each other, in one portion of said rack member with said second light filter member being disposed in a plane at right angles to the plane of said first filter member,
an actuating member slidably mounted in said housing having a finger actuator portion extending through said housing;
said actuating member being operatively connected to said aperture rack so that a physician may selectively position at least one of said light filter members in the beam of light transmitted to the patient's eye;
said actuating member being operatively connected to said aperture rack so that when one of said first and second filter members is positioned in the light transmitted to the patient's eye, the second filter is positioned in the viewing passage to the physician's eye to filter light reflected from the patient's eye.

9. An ophthalmoscope as claimed in claim 8 wherein said rack member has disposed therein three filter openings; a different light filter member disposed in each of said openings and at least one other light filter member disposed adjacent to and in perpendicular relationship to one of said three light filter members.

10. An ophthalmoscope as claimed in claim 8 wherein said aperture rack member is mounted in said housing adjacent the intersection of the viewing passage and the light transmission passage so that a first light filter carried in said rack member may selectively be positioned in the light transmitted to the patient's eye and a second light filter member carried in said rack member will be simultaneously positioned in said viewing passage to filter light reflected from the patient's eye to the physician's eye.

11. A device as described in claim 8 wherein said plurality of light filter members comprise a red free filter member, a first light polarizing filter member, and a clear filter member mounted in the base of said rack member for selective positioning in the light transmitted to the patient's eye; and
a second light polarizing filter mounted adjacent to and at right angles to said first light polarizing filter in said rack member.

12. A device as claimed in claim 8 wherein said rack member comprises a flat plate having three circular openings therein, a rack gear along one edge, and a polarizing filter mounting slot along the edge opposite said gear rack; and wherein said actuating member comprises a slide bar having thereon a finger actuator portion and a rack gear portion; and a spur gear rotatably mounted in said frame to operatively connect said rack member to said actuating member.

13. A device as claimed in claim 8 wherein said polarizing light filter members are disposed at right angles to each other.

14. A device as claimed in claim 8 wherein said polarizing light members are mounted with the polarization axis of one disposed perpendicular to the polarization axis of the other.

15. In an ophthalmoscope having a housing, a viewing passage therethrough, light source, lens and mirror light transmitting means disposed to transmit a beam of light from said source through said viewing passage to the patient's eye in virtual co-axial relationship with said viewing passage; means for selectively reducing glare in the light reflected from the patient's eye comprising:
an aperture rack slidably mounted in said housing;
a pair of polarizing light filtering members mounted in said aperture rack;
single actuating means operatively connected to said polarizing light filtering members for selectively positioning said filtering elements into and out of the light and viewing paths;
so that when positioned in said paths, one of said polarizing light filter elements is disposed in the beam of light to illuminate the patient's eye and the other of said polarizing light filter elements is disposed in the viewing passage to filter the light reflected from the patient's eye so that reflected glare from the cornea of the eye is reduced to permit a more effective examination of the retina of the eye.

* * * * *